Sept. 25, 1962 R. S. MOORE Plant Pat. 2,176
MINIATURE ROSE PLANT
Filed Aug. 17, 1961
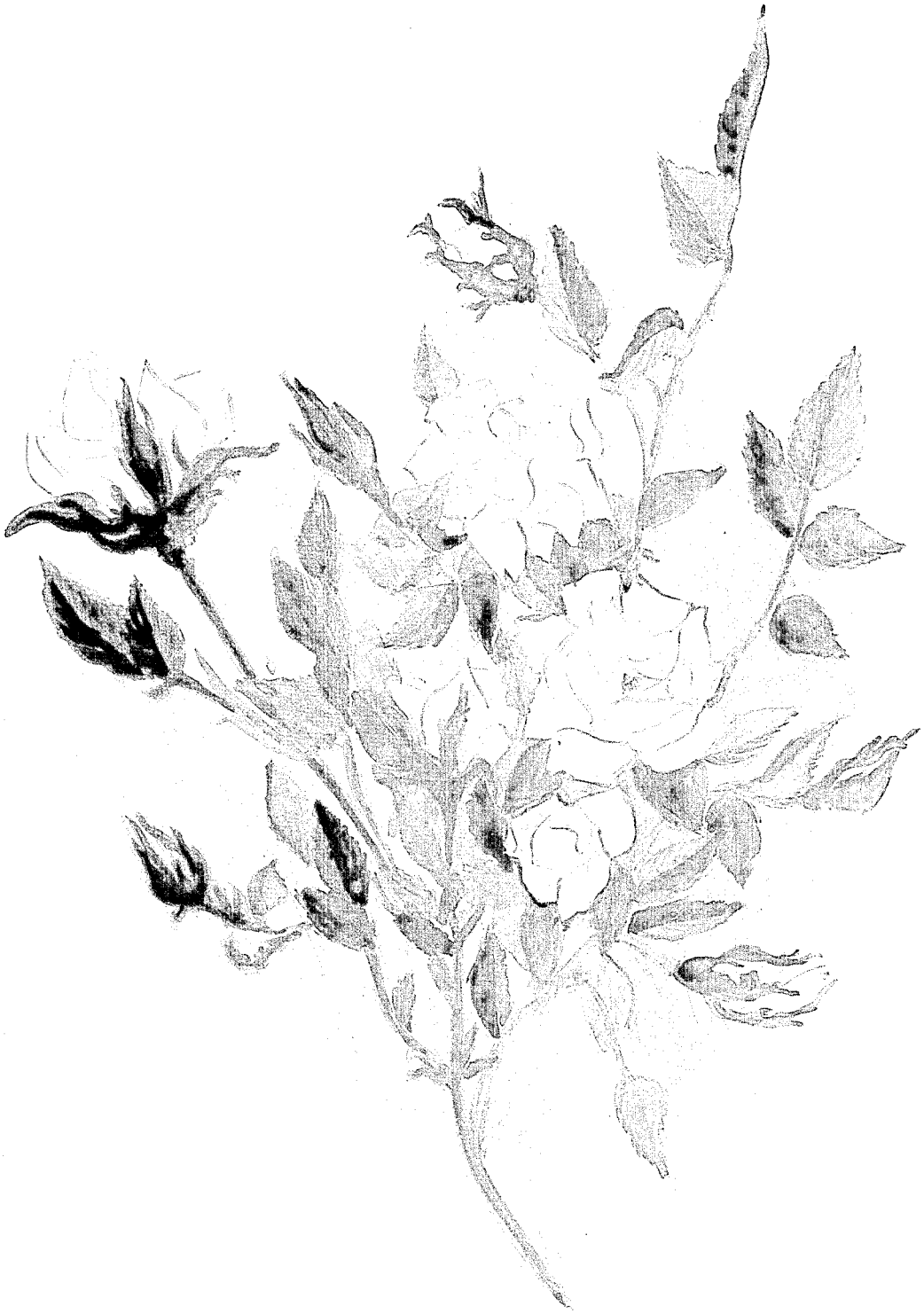
WITNESS
Jeanette Copley
INVENTOR
Ralph S. Moore
Webster & Webster
ATTYS.

United States Patent Office

Plant Pat. 2,176
Patented Sept. 25, 1962

2,176
MINIATURE ROSE PLANT

Ralph S. Moore, 2519 E. Mineral King, Visalia, Calif.

Filed Aug. 17, 1961, Ser. No. 132,248
1 Claim. (Cl. 47—61)

This invention relates to a new and distinct variety of hybrid miniature rose plant of hardy, upright, much branched, climbing type; the variety being particularly characterized by small flowers which have a basic yellow color. However, at times, and dependent on climatic conditions, the yellow is partially overlaid or shaded with red. In clear warm weather, as in the summer, the flowers are usually yellow in their entire coloring, but in cooler weather with a few cloudy days, as in the spring and fall, the red tones appear with the basic yellow and which gives the effect of a small Talisman rose. The basic yellow color persists in all weather and holds until petiole fall.

The present variety is believed to be the first climbing miniature rose plant having flowers colored as described above; such variety—in plant habit—being generally similar to the Climbing Jackie (unpatented) of identical parentage. These two varieties are, however, distinct from each other in that the instant variety has yellow flowers sometimes shaded with red, whereas the Climbing Jackie has flowers that are more double and a soft creamy color.

The present variety of miniature rose plant is additionally characterized as being easily propagated by budding or soft wood cuttings; good growth and plant habits, with the plants being hardy and often starting to bloom when not over 5" to 8" tall—even in small pots in the nursery; and general bud and flower form that is quite similar to the larger hybrid tea rose.

The variety was originated by me in my nursery located at Visalia, California, under conditions of careful control and observation, as a cross between Golden Glow (United States Plant Patent No. 263) as the seed parent, and Zee (unpatented) as the pollen parent; Zee being a miniature rose variety heretofore originated by me, used only for rose plant breeding, and which has not been introduced to the trade.

Subsequent to origination of the variety I successfully asexually reproduced it, in my nursery located as aforesaid, by budding as well as cuttings; the reproductions having run true in all respects.

The FIGURE of the drawings illustrates a spray, including foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; climbing; seedling; outdoors; garden decoration; cut flowers.
Class: Hybrid miniature.

*Flowers*

Continuity: Continuous.
Fragrance: Moderate.
Flowers borne: Two to three, several to stem, in irregular rounded cluster, on strong medium length stems.
Quantity of Bloom: Abundant, outdoors.
Bud:
*Peduncle.*—Long, slender; erect; stiff; medium green; smooth.
*Before calyx breaks.*—Size—medium to small. Form—pointed; with foliaceous appendages on the surface of the bud; with foliaceous parts extending beyond the tip of the bud equal to one-half of its length. Color—medium green—slightly deeper than peduncle.
*As calyx breaks.*—Color—yellow, often splashed or tipped orange.
*As first petal opens.*—Size—small to medium. Form—pointed, ovoid. Color: outside—yellow, often shaded orange near tip; inside—deeper yellow, often tinted or splashed with orange or red on outer half of petal. Opening—opens well.
Bloom:
*Size when fully open.*—Small, averaging 1¼" to 1½".
*Petalage.*—Double, with from 25 to 35 (sometimes up to 50) petals arranged regularly.
*Form.*—Full, high center at first, becoming open. Petals at first, and at maturity, loosely rolled outward.
Petals: Leathery; satiny, both inside and outside.
*Shape.*—Outside—oblanceolate. Intermediate—obovate or lanceolate. Inside—lanceolate.
*Color.*—Newly opened flower on plant grown outdoors (July 1961): outside and intermediate petals, both outside surfaces and inside surfaces, Canary Yellow, 2/1, partially overlaid or shaded on outer one-half of petals with Saturn Red, 13/1; inner petal, both outside and inside surfaces, Canary Yellow, 2/1, partially overlaid or shaded on the outer one-half of the petal with a lighter red or orange. A flower open for three days on a plant grown outdoors (July 1961).—Outside petal: outside surface—Canary Yellow, 2/1 at base, shading through 2/2, shading into Buttercup Yellow, 5/2; inside surface—Canary Yellow, 2/1 at base, shading through 2/2, with outer one-half of petal shading into Tangerine Orange, 9/3—9/2. Inner petal—both outside and inside surfaces, Canary Yellow, 2/1 at base, shading through 2/2 to Buttercup Yellow, 5/2.
*General color effect.*—Newly opened flower—entire yellow, or yellow shaded with red, dependent on weather. Three days open—like color, but slightly lighter.
*Behavior.*—Drop off cleanly. Affected by weather as follows: color variable or changeable as described.
*Flower longevity (May-June).*—Bush in garden—three to four days. Cut flowers kept at living room temperatures—two to four days.

*Reproductive Organs*

Stamens: Medium to many; arranged regularly.
Filaments: Medium length; most with anthers; deep yellow.
Anthers: Medium size; open at various times; yellow.
Pollen: Sparse; yellow.
Pistils: Medium number.
Styles: Even; medium length; medium thickness; bunched.
Stigma: Greenish-white.
Ovaries: All enclosed in calyx.
Hips: Short; globular; smooth; walls thin; very few appear. The variety almost completely female-seterile.
Sepals: Permanent; long; straight; spear shaped; recurved. Green, changing to brown.
Seeds: Very few and did not sprout.

*Plant*

Foliage:
*Leaves.*—Compound of 5 to 7 leaflets; normal abundance; moderately small; moderately heavy.
*Leaflets.*—Shape—lanceolate. Apex—acute. Base—round. Margin—serrate. Color: Mature—upper surface—normal green; under surface—normal green. Young—upper surface—normal green; under surface—normal green, tinted reddish or purplish. Rachis—upper side—grooved, with a few prickles; under side—prickly, with two or three small thorns. Stipules—medium length; moderately narrow, with medium length points turning out at an angle of about 45 degrees or less.

Growth:

*Habit.*—Upright; climbing; much branched.

*Growth.*—Moderate to vigorous.

*Canes.*—Medium strength.

*Main stems.* — Color — green. Thorns — several; mainly straight—hooked slightly down; base oval. Prickles—none to few. Hairs—none.

*Branches.*—Color—green. Thorns—several; hooked very slightly downward; base oval. Prickles—none. Hairs—none.

*New shoots.*—Color—bright green. Thorns—several; base oval. Prickles—none. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of rose plant of the hybrid miniature class and of hardy, upright, much branched, climbing type, as illustrated and described, characterized—in comparison to the Climbing Jackie—by generally similar plant habit but by dissimilarity in color of the flowers; such color varying, dependent on the weather, from an entire yellow to a yellow shaded with red.

No references cited.